United States Patent
Wilkins

(10) Patent No.: US 10,123,702 B1
(45) Date of Patent: Nov. 13, 2018

(54) PATIENT MONITORING SYSTEM

(71) Applicant: Jennifer Wilkins, Mechanicsburg, PA (US)

(72) Inventor: Jennifer Wilkins, Mechanicsburg, PA (US)

( * ) Notice: Subject to any disclaimer, the term of this patent is extended or adjusted under 35 U.S.C. 154(b) by 0 days.

(21) Appl. No.: 15/692,280

(22) Filed: Aug. 31, 2017

(51) Int. Cl.
| G08B 1/08 | (2006.01) |
| A61B 5/00 | (2006.01) |
| A61B 5/024 | (2006.01) |
| G08B 21/18 | (2006.01) |
| G16H 40/63 | (2018.01) |

(52) U.S. Cl.
CPC ........ *A61B 5/0002* (2013.01); *A61B 5/02438* (2013.01); *G08B 21/18* (2013.01); *G16H 40/63* (2018.01)

(58) Field of Classification Search
CPC . G06F 19/3418; A61B 5/0002; A61B 5/0015; A61B 5/0022; A61B 5/02438; G16H 40/63; G08B 21/18
USPC ..... 340/573.1, 539.11, 539.12; 600/300, 301
See application file for complete search history.

(56) References Cited

U.S. PATENT DOCUMENTS

| 6,102,856 | A | 8/2000 | Groff et al. | |
| 6,547,728 | B1 | 4/2003 | Cornuejois | |
| 7,400,257 | B2* | 7/2008 | Rivas | A61B 5/0022 340/539.12 |
| 8,233,969 | B2 | 7/2012 | Muhlsteff et al. | |
| 8,591,411 | B2* | 11/2013 | Banet | A61B 5/0002 600/300 |
| D753,314 | S | 4/2016 | Stivoric et al. | |
| 2004/0130446 | A1 | 7/2004 | Chen et al. | |
| 2005/0106713 | A1 | 5/2005 | Phan et al. | |
| 2005/0250440 | A1 | 11/2005 | Zhou et al. | |
| 2011/0028821 | A1 | 2/2011 | Bojovic et al. | |
| 2013/0099918 | A1* | 4/2013 | Dunst | A61B 5/0002 340/539.12 |
| 2015/0057512 | A1* | 2/2015 | Kapoor | A61B 5/0205 600/324 |
| 2015/0302539 | A1* | 10/2015 | Mazar | G08B 21/0211 705/3 |
| 2016/0210416 | A1* | 7/2016 | Whitehurst | G06F 19/3418 |

FOREIGN PATENT DOCUMENTS

WO    WO2011014833    2/2011

* cited by examiner

*Primary Examiner* — Thomas Mullen

(57) ABSTRACT

A patient monitoring system includes an electronic device that may be manipulated by a first user. The electronic device has a first transceiver. A monitoring unit is worn on a second user thereby facilitating the monitoring unit to detect vital signs of the second user. The monitoring unit is in wireless electrical communication with the electronic device via the Internet or the like. Moreover, the monitoring unit selectively generates an alarm sequence when the monitoring unit detects that the vital signs have deviated from a pre-determined normal state. The electronic device generates an audible alarm when the monitoring unit generates the alarm sequence. In this way the electronic device notifies the first user that the second user is experiencing a medical emergency.

13 Claims, 2 Drawing Sheets

PATIENT MONITORING SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to monitoring devices and more particularly pertains to a new monitoring device facilitating a family member to remotely monitor vital signs of a person in a medical care facility.

BRIEF SUMMARY OF THE INVENTION

An embodiment of the disclosure meets the needs presented above by generally comprising an electronic device that may be manipulated by a first user. The electronic device has a first transceiver. A monitoring unit is worn on a second user thereby facilitating the monitoring unit to detect vital signs of the second user. The monitoring unit is in wireless electrical communication with the electronic device via the Internet or the like. Moreover, the monitoring unit selectively generates an alarm sequence when the monitoring unit detects that the vital signs have deviated from a pre-determined normal state. The electronic device generates an audible alarm when the monitoring unit generates the alarm sequence. In this way the electronic device notifies the first user that the second user is experiencing a medical emergency.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
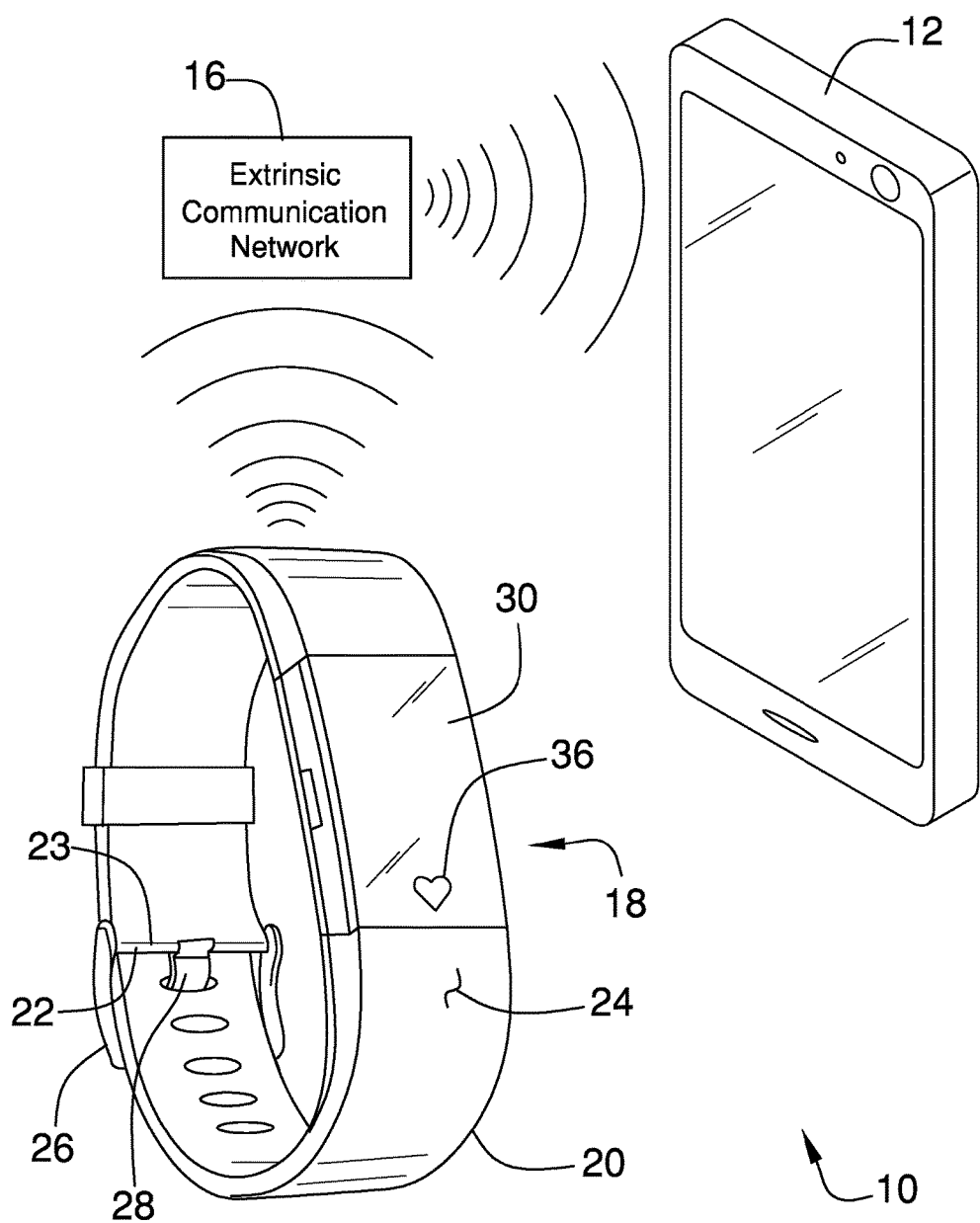
FIG. 1 is a perspective view of a patient monitoring system according to an embodiment of the disclosure.
Figure 2:
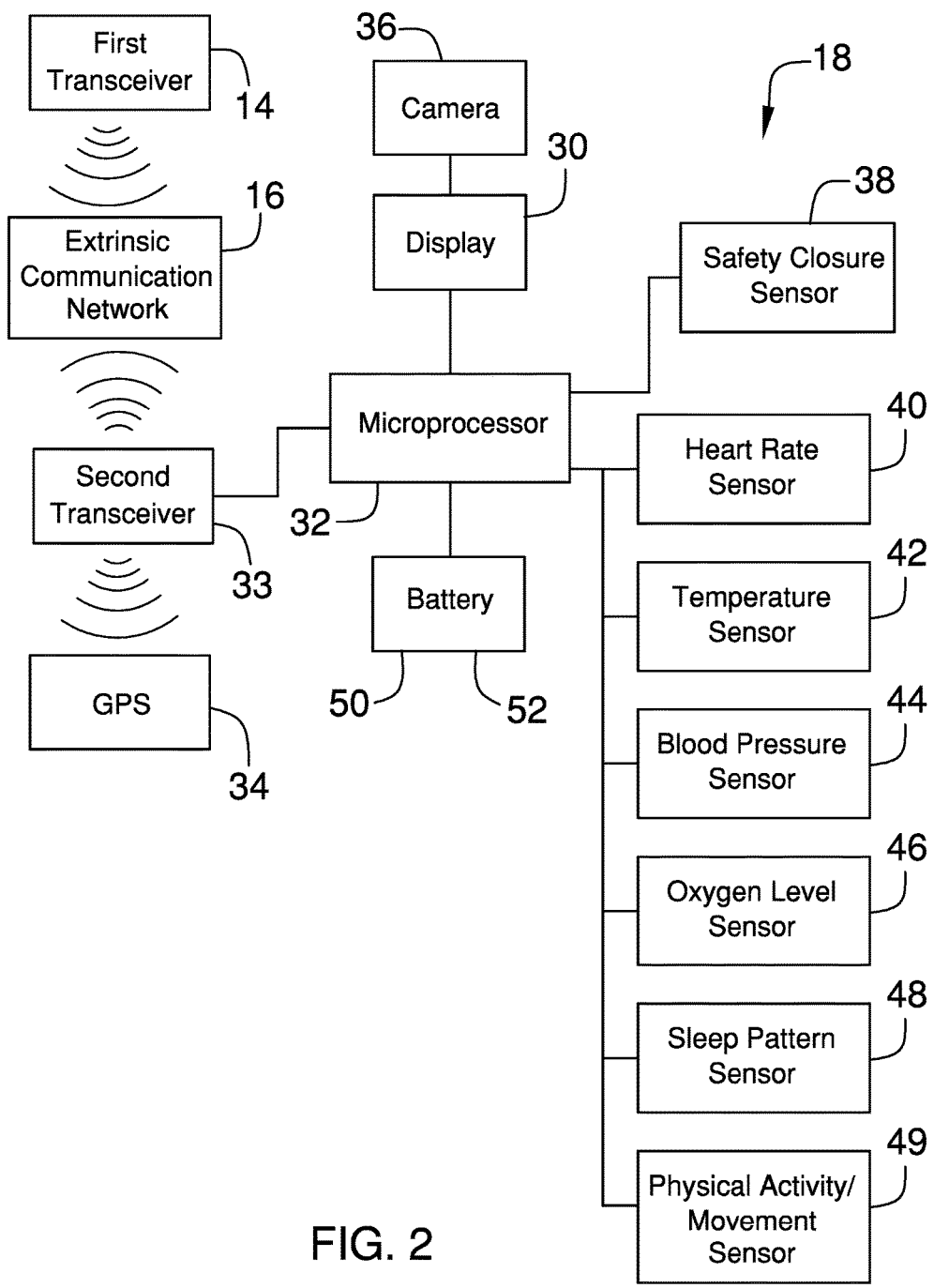
FIG. 2 is a schematic view of an embodiment of the disclosure.

With reference now to the drawings, and in particular to FIGS. 1 through 2 thereof, a new monitoring device embodying the principles and concepts of an embodiment of the disclosure and generally designated by the reference numeral 10 will be described.

As best illustrated in FIGS. 1 through 2, the patient monitoring system 10 generally comprises an electronic device 12 that is manipulated by a first user. The electronic device 12 has a first transceiver 14. The first transceiver 14 may be a radio frequency transceiver or the like. Additionally, the first transceiver 14 may be in electrical communication with an extrinsic communication network 16 such as the Internet or the like. The electronic device 12 may be a smart phone or the like and the electronic device 12 may store a control program.

A monitoring unit 18 is provided and the monitoring unit 18 is worn on a second user thereby facilitating the monitoring unit 18 to detect vital signs of the second user. The monitoring unit 18 is in wireless electrical communication with the electronic device 12. Moreover, the monitoring unit 18 selectively generates an alarm sequence when the monitoring unit 18 detects that the vital signs have deviated from a pre-determined normal state. The electronic device 12 generates an audible alarm when the monitoring unit 18 generates the alarm sequence. In this way the electronic device 12 notifies the first user that the second user is experiencing a medical emergency. The second user may be a patient in a health care environment or other person incapable of caring for themselves. The first user may be a person that is remotely located with respect to the second user, such as a family member or the like.

The monitoring unit 18 comprises a bracelet 20 that may be worn around a wrist. The bracelet 20 has a first end 22, a second end 23 and a first surface 24 extending therebetween. A first attachment 26 is coupled to the first end 22 and the first attachment 26 is selectively manipulated. The first attachment 26 may be any mechanical attachment that requires one hand to manipulate.

A second attachment 28 is coupled to the second end 23 and the second attachment 28 is selectively manipulated. The second attachment 28 is selectively matable to the first attachment 26 when each of the first 26 and second 28 attachments is manipulated. The second attachment 28 may be any mechanical attachment that requires one hand to manipulate. Thus, two hands are required to remove the bracelet 20 from the wrist. In this way an Alzheimer's patient or the like is inhibited from inadvertently removing the bracelet 20.

A display 30 is coupled to the first surface 24 of the bracelet 20 such that the display 30 is visible when the bracelet 20 is worn. The display 30 may be an LED display 30 or the like. A processor 32 is coupled to the bracelet 20 and the processor 32 selectively generates the alarm sequence. The display 30 is electrically coupled to the processor 32 and the processor 32 may be an electronic processor or the like. The display 30 may display indicia relating to operational parameters of the monitoring unit.

A second transceiver 33 is coupled to the bracelet 20 and the second transceiver 33 is electrically coupled to the processor 32. The second transceiver 33 is in electrical communication with the first transceiver 14 such that the electronic device 12 receives the alarm sequence from the processor 32. Additionally, the second transceiver 33 is in electrical communication with a global positioning system (GPS). In this way the second transceiver 33 receives a physical location of the bracelet 20 from the GPS 34. The second transceiver 33 may be a radio frequency transceiver or the like and the second transceiver 33 is in electrical communication with the extrinsic communication network 16. In this way the second transceiver 33 is in electrical communication with the first transceiver 14 regardless of the distance between the first and second users.

A camera 36 is coupled to the first surface 24 of the bracelet 20 to capture images of the second user's environment. The camera 36 is electrically coupled to the processor 32. The camera 36 may be a digital camera and the camera 36 may capture still images and video.

A closure sensor 38 is coupled to the first attachment 26 and the closure sensor 38 is electrically coupled to the processor 32. The closure sensor 38 senses whether the second attachment 28 is coupled to the first attachment. Moreover, the processor 32 generates the alarm sequence when the closure sensor 38 senses that the second attachment 28 has been uncoupled from the first attachment 26. In this way the first user is notified when the bracelet 20 is removed from the second user. The closure sensor 38 may be an electronic sensor including, but not being limited to, magnetic sensors and mechanical sensors.

A heart rate sensor 40 is coupled to the bracelet 20. The heart rate sensor 40 is in physical contact with the second user thereby facilitating the heart rate sensor 40 to sense the second user's heart rate when the bracelet 20 is worn. The heart rate sensor 40 is electrically coupled to the processor 32. The processor 32 generates the alarm sequence when the heart rate sensor 40 senses the second user's heart rate has deviated from a pre-determined heart rate. The heart rate sensor 40 may be an electronic heart rate sensor 40 or the like.

A temperature sensor 42 is coupled to the bracelet 20. The temperature sensor 42 is in physical contact with the second user thereby facilitating the temperature sensor 42 to sense the second user's temperature when the bracelet 20 is worn. The temperature sensor 42 is electrically coupled to the processor 32. The processor 32 generates the alarm sequence when the temperature sensor 42 senses the second user's temperature has deviated from a pre-determined temperature range. Moreover, the temperature sensor 42 may be an electronic temperature sensor 42 or the like.

A blood pressure sensor 44 is coupled to the bracelet 20. The blood pressure sensor 44 is in physical contact with the second user thereby facilitating the blood pressure sensor 44 to sense the second user's blood pressure when the bracelet 20 is worn. The blood pressure sensor 44 is electrically coupled to the processor 32. Additionally, the processor 32 generates the alarm sequence when the blood pressure sensor 44 senses the second user's blood pressure has deviated from a pre-determined blood pressure range. The blood pressure sensor 44 may be an electronic blood pressure sensor 44 or the like. Moreover, the blood pressure sensor 44 may rely on the bracelet 20 to act as a cuff for sensing the blood pressure in the wrist.

An oxygen level sensor 46 is coupled to the bracelet 20. The oxygen level sensor 46 is in physical contact with the second user thereby facilitating the oxygen level sensor 46 to sense the second user's oxygen level when the bracelet 20 is worn. The oxygen level sensor 46 is electrically coupled to the processor 32. The processor 32 generates the alarm sequence when the oxygen level sensor 46 senses the second user's oxygen level has deviated from a pre-determined oxygen level range. The oxygen level sensor 46 may be an electronic blood oxygen sensor or the like.

A sleep pattern sensor 48 is coupled to the bracelet 20. The sleep pattern sensor 48 is in physical contact with the second user thereby facilitating the sleep pattern sensor 48 to sense the second user's sleep pattern when the bracelet 20 is worn. The sleep pattern sensor 48 is electrically coupled to the processor 32. Moreover, the processor 32 generates the alarm sequence when the sleep pattern sensor 48 senses the second user's sleep pattern has deviated from a pre-determined sleep pattern range. The sleep pattern sensor 48 may be an electronic sleep pattern sensor 48 or the like.

A motion sensor 49 is coupled to the bracelet 20. The motion sensor 49 is in physical contact with the second user thereby facilitating the motion sensor 49 to sense the second user's motion when the bracelet 20 is worn. The motion sensor 49 is electrically coupled to the processor 32 such that the electronic device 12 may track the second user's motion. A power supply 50 is coupled to the bracelet 20 and the power supply 50 is electrically coupled to the processor 32. The power supply 50 comprises at least one battery 52.

In use, the bracelet 20 is placed around the second user's wrist when the second user is admitted into a medical care facility, such as a hospital, nursing home and other long term care facility. The first transceiver 14 in the electronic device 12 is synched with the second transceiver 33 via the extrinsic communication network 16. In this way the first transceiver 14 is in remote communication with the second transceiver 33. The processor 32 generates the alarm sequence when the second user's heart rate, body temperature, blood pressure and oxygen levels fall above or below the corresponding pre-determined range. Additionally, the processor 32 generates the alarm sequence when the closure sensor 38 senses that the first attachment 26 is uncoupled from the second attachment 28.

The electronic device 12 emits the audible alarm when the processor 32 generates the alarm sequence. In this way the first user is remotely notified that the second user is experiencing a potential medical emergency. Moreover, the first user may contact the medical care facility to verify that the medical care facility is responding to the potential medical emergency. The motion sensor 49 tracks the second user's movement thereby facilitating the first user to verify that the medical care facility is moving the second user according to established guidelines. Additionally, the motion tracker facilitates the first user to locate the second user when the second user suffers from dementia and becomes lost.

With respect to the above description then, it is to be realized that the optimum dimensional relationships for the parts of an embodiment enabled by the disclosure, to include variations in size, materials, shape, form, function and manner of operation, system and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A patient monitoring system comprising:
an electronic device being configured to be manipulated by a first user, said electronic device having a first transceiver;
a monitoring unit being configured to be worn on a second user thereby facilitating said monitoring unit to detect a vital sign of the second user, said monitoring unit being in wireless electrical communication with said electronic device via the Internet, said monitoring unit selectively generating an alarm trigger when said monitoring unit detects that the vital sign has deviated from a pre-determined normal state for the vital sign, and said electronic device generating an audible alarm when said said electronic device receives said alarm trigger generated by said monitoring unit, said electronic device being configured to notify the first user that the second user is experiencing a medical emergency, said monitoring unit comprising a bracelet being configured to be worn around a wrist, said bracelet having a first end, a second end and a first surface extending therebetween; and
a first attachment being coupled to said first end wherein said first attachment is configured to be manipulated.

2. The system according to claim 1, further comprising a processor being coupled to said bracelet, said processor selectively generating said alarm trigger.

3. The system according to claim 2, further comprising a display being coupled to said first surface of said bracelet wherein said display is configured to be visible when said bracelet is worn, said display being electrically coupled to said processor.

4. The system according to claim 1, further comprising a second transceiver being coupled to said bracelet, said second transceiver being electrically coupled to a processor coupled to said bracelet, said second transceiver being in electrical communication with said first transceiver such that said electronic device receives said alarm trigger from said processor, said second transceiver being configured to be in electrical communication with a global positioning system (GPS) wherein said second transceiver is configured to receive a signal indicative of a physical location of said bracelet from the GPS.

5. The system according to claim 1, further comprising:
a second attachment being coupled to said second end wherein said second attachment is configured to be manipulated, said second attachment being selectively matable to said first attachment;
a processor being coupled to said bracelet, said processor selectively generating said alarm trigger; and
a closure sensor being coupled to said first attachment, said closure sensor being electrically coupled to said processor, said closure sensor sensing whether said second attachment is coupled to said first attachment, said processor generating said alarm trigger when said closure sensor senses that said second attachment has been uncoupled from said first attachment.

6. The system according to claim 1, further comprising a heart rate sensor being coupled to said bracelet wherein said heart rate sensor is configured to be in physical contact with the second user thereby facilitating said heart rate sensor to sense the second user's heart rate when said bracelet is worn, said heart rate sensor being electrically coupled to a processor coupled to said bracelet, said processor generating said alarm trigger when said heart rate sensor senses the second user's heart rate has deviated from a pre-determined heart rate.

7. The system according to claim 1, further comprising a temperature sensor being coupled to said bracelet wherein said temperature sensor is configured to be in physical contact with the second user thereby facilitating said temperature sensor to sense the second user's temperature when said bracelet is worn, said temperature sensor being electrically coupled to a processor coupled to said bracelet, said processor generating said alarm trigger when said temperature sensor senses the second user's temperature has deviated from a pre-determined temperature range.

8. The system according to claim 1, further comprising a blood pressure sensor being coupled to said bracelet wherein said blood pressure sensor is configured to be in physical contact with the second user thereby facilitating said blood pressure sensor to sense the second user's blood pressure when said bracelet is worn, said blood pressure sensor being electrically coupled to a processor coupled to said bracelet, said processor generating said alarm trigger when said blood pressure sensor senses the second user's blood pressure has deviated from a pre-determined blood pressure range.

9. The system according to claim 1, further comprising an oxygen level sensor being coupled to said bracelet wherein said oxygen level sensor is configured to be in physical contact with the second user thereby facilitating said oxygen level sensor to sense the second user's oxygen level when said bracelet is worn, said oxygen level sensor being electrically coupled to a processor coupled to said bracelet processor, said processor generating said alarm trigger when said oxygen level sensor senses the second user's oxygen level has deviated from a pre-determined oxygen level range.

10. The system according to claim 1, further comprising a sleep pattern sensor being coupled to said bracelet wherein said sleep pattern sensor is configured to be in physical contact with the second user thereby facilitating said sleep pattern sensor to sense the second user's sleep pattern when said bracelet is worn, said sleep pattern sensor being electrically coupled to a processor coupled to said bracelet processor, said processor generating said alarm trigger when said sleep pattern sensor senses the second user's sleep pattern has deviated from a pre-determined sleep pattern range.

11. The system according to claim 1, further comprising a motion sensor being coupled to said bracelet wherein said motion sensor is configured to be in physical contact with the second user thereby facilitating said motion sensor to sense the second user's motion when said bracelet is worn, said motion sensor being electrically coupled to a processor coupled to said bracelet wherein said electronic device is configured to track the second user's motion.

12. The system according to claim 1, further comprising a power supply being coupled to said bracelet, said power supply being electrically coupled to a processor coupled to said bracelet, said power supply comprising at least one battery.

13. A patient monitoring system comprising:
an electronic device being configured to be manipulated by a first user, said electronic device having a first transceiver; and
a monitoring unit being configured to be worn on a second user thereby facilitating said monitoring unit to detect a vital sign of the second user, said monitoring unit being in wireless electrical communication with said electronic device via the Internet, said monitoring unit selectively generating an alarm trigger when said monitoring unit detects that the vital sign has deviated from a pre-determined normal state for the vital sign, said electronic device generating an audible alarm when said said electronic device receives said alarm trigger generated by said monitoring unit wherein said electronic device is configured to notify the first user that the second user is experiencing a medical emergency, said monitoring unit comprising:
a bracelet being configured to be worn around a wrist, said bracelet having a first end, a second end and a first surface extending therebetween,
a first attachment being coupled to said first end wherein said first attachment is configured to be manipulated,
a second attachment being coupled to said second end wherein said second attachment is configured to be manipulated, said second attachment being selectively matable to said first attachment,
a display being coupled to said first surface of said bracelet wherein said display is configured to be visible when said bracelet is worn,
a processor being coupled to said bracelet, said processor selectively generating said alarm trigger, said display being electrically coupled to said processor,
a second transceiver being coupled to said bracelet, said second transceiver being electrically coupled to said processor, said second transceiver being in electrical communication with said first transceiver such that said electronic device receives said alarm sequence from said processor, said second transceiver being configured to be in electrical communication with a global positioning system (GPS) wherein said second transceiver is configured to receive a signal indicative of a physical location of said bracelet from the GPS,
a camera being coupled to said first surface of said bracelet wherein said camera is configured to capture images of the first user's environment, said camera being electrically coupled to said processor,
a closure sensor being coupled to said first attachment, said closure sensor being electrically coupled to said processor, said closure sensor sensing whether said second attachment is coupled to said first attachment, said processor generating said alarm trigger when said closure sensor senses that said second attachment has been uncoupled from said first attachment, a heart rate sensor being coupled to said bracelet wherein said heart rate sensor is configured to be in physical contact with the second user thereby facilitating said heart rate sensor to sense the second user's heart rate when said bracelet is worn, said heart rate sensor being electrically coupled to said processor, said processor generating said alarm trigger when said heart rate sensor senses the second user's heart rate has deviated from a pre-determined heart rate,
a temperature sensor being coupled to said bracelet wherein said temperature sensor is configured to be in physical contact with the second user thereby facilitating said temperature sensor to sense the second user's temperature when said bracelet is worn, said temperature sensor being electrically coupled to said processor, said processor generating said alarm trigger when said temperature sensor senses the second user's temperature has deviated from a pre-determined temperature range,
a blood pressure sensor being coupled to said bracelet wherein said blood pressure sensor is configured to be in physical contact with the second user thereby facilitating said blood pressure sensor to sense the second user's blood pressure when said bracelet is worn, said blood pressure sensor being electrically coupled to said processor, said processor generating said alarm trigger when said blood pressure sensor senses the second user's blood pressure has deviated from a pre-determined blood pressure range,
an oxygen level sensor being coupled to said bracelet wherein said oxygen level sensor is configured to be in physical contact with the second user thereby facilitating said oxygen level sensor to sense the second user's oxygen level when said bracelet is worn, said oxygen level sensor being electrically coupled to said processor, said processor generating said alarm trigger when said oxygen level sensor senses the second user's oxygen level has deviated from a pre-determined oxygen level range,
a sleep pattern sensor being coupled to said bracelet wherein said sleep pattern sensor is configured to be in physical contact with the second user thereby facilitating said sleep pattern sensor to sense the second user's sleep pattern when said bracelet is worn, said sleep pattern sensor being electrically coupled to said processor, said processor generating said alarm trigger when said sleep pattern sensor senses the second user's sleep pattern has deviated from a pre-determined sleep pattern range,
a motion sensor being coupled to said bracelet wherein said motion sensor is configured to be in physical contact with the second user thereby facilitating said motion sensor to sense the second user's motion when said bracelet is worn, said motion sensor being electrically coupled to said processor wherein said electronic device is configured to track the second user's motion, and
a power supply being coupled to said bracelet, said power supply being electrically coupled to said processor, said power supply comprising at least one battery.

* * * * *